United States Patent [19]

Büchel et al.

[11] 3,940,415
[45] Feb. 24, 1976

[54] 1-(IMIDAZOLYL-1)-2-ARYLOXY-3-HYDROXY-ALKANES

[75] Inventors: Karl-Heinz Büchel; Wolfgang Krämer, both of Wuppertal; Paul-Ernst Frohberger; Hans Scheinpflug, both of Leverkusen, all of Germany

[73] Assignee: Bayer Aktiengesellschaft, Leverkusen, Germany

[22] Filed: Sept. 30, 1974

[21] Appl. No.: 510,833

[30] Foreign Application Priority Data
Oct. 5, 1973  Germany............................ 2350123

[52] U.S. Cl................................ 260/309; 424/273
[51] Int. Cl.². ........................................ C07D 233/60
[58] Field of Search .................................. 260/309

[56] References Cited
UNITED STATES PATENTS

| | | | |
|---|---|---|---|
| 3,468,902 | 9/1969 | Beaman et al. | 260/309 |
| 3,531,494 | 9/1970 | Adolphi et al. | 260/309 |
| 3,575,999 | 4/1971 | Godefroi et al. | 260/309 |
| 3,658,813 | 4/1972 | Godefroi et al. | 260/309 |
| 3,682,951 | 8/1972 | Kreider | 260/309 |
| 3,717,655 | 2/1973 | Godefroi et al. | 260/309 |
| 3,796,704 | 3/1974 | Metzger et al. | 260/309 |

OTHER PUBLICATIONS
Sunjic et al., Chem. Abst., 1969, Vol. 70, No. 3945t.

*Primary Examiner*—Natalie Trousof
*Attorney, Agent, or Firm*—Burgess, Dinklage & Sprung

[57] ABSTRACT 1-(imidazolyl-1')-2-aryloxy-3-hydroxy-alkanes of the formula

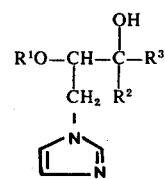

in which
 $R^1$ is optionally substituted aryl,
 $R^2$ is hydrogen, alkyl, cycloalkyl, alkenyl, optionally substituted aryl or optionally substituted aralkyl, and
 $R^3$ is alkyl or cycloalkyl, or can be hydrogen if $R^2$ is not hydrogen,
and their salts, which possess fungicidal properties.

5 Claims, No Drawings

1-(IMIDAZOLYL-1)-2-ARYLOXY-3-HYDROXY-ALKANES

The present invention relates to and has for its objects the provision of particular new 1-(imidazolyl-1')-2-aryloxy-3-hydroxy-alkanes, which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has been disclosed in Pat. 3,321,366 that tritylimidazoles, such as triphenylmethyl-imidazole (Compound A) or (phenyl-bis-chlorophenyl-methyl)-imidazole (Compound B), possess a good fungicidal activity. However, their action is not always entirely satisfactory, especially if low amounts and low concentrations are used. Furthermore, it is generally known that zinc ethylene-1,2-bis-dithiocarbamate (Compound C) exhibits an activity against fungal diseases of cereals. Its action, too, is not always satisfactory if low amounts and low concentrations are used.

The present invention provides, as new compounds, the 1-propyl-imidazolyl derivatives of the general formula

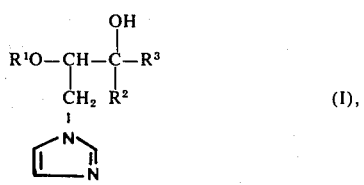

(I), in which
R$^1$ is optionally substituted aryl,
R$^2$ is hydrogen, alkyl, cycloalkyl, alkenyl, optionally substituted aryl or optionally substituted aralkyl, and
R$^3$ is alkyl or cycloalkyl, or can be hydrogen if R$^2$ is not hydrogen,
and their salts.

Surprisingly, the active compounds according to the invention exhibit a substantially greater fungicidal action than the known compound triphenylmethyl-imidazole and the other chemically nearest active compounds. The active compounds according to the invention thus represent an enrichment of the art.

Preferably R$^1$ is an optionally monosubstituted or poly- (e.g., di-) substituted aryl radical with 6 to 10 carbon atoms, especially with 6 carbon atoms, the preferred substituents being halogen, especially fluorine, chlorine or bromine, straight-chain or branched alkyl with 1 to 6, especially 1 to 4, carbon atoms, alkoxy, alkylthio and alkylsulfonyl with 1 to 4, especially 1 or 2, carbon atoms, halogenoalkyl with 1 or 2 carbon atoms and 1 to 5 halogen atoms, especially fluorine and chlorine, halogenoalkoxy and halogenoalkylthio with 1 or 2 carbon atoms and 3 to 5 halogen atoms, especially fluorine and chlorine, for example chlorodifluoromethylthio and chlorodifluoromethoxy, alkoxycarbonyl with 1 to 4 carbon atoms in the alkoxy moiety, phenyl in the o- and p-position, amino and nitro; R$^2$ is hydrogen, alkyl with up to 6, especially up to 4, carbon atoms, or aralkyl with 6 to 10 carbon atoms in the aryl moiety, which may be substituted (e.g., mono-), and 1 or 2 carbon atoms in the alkyl moiety, preferred substituents on the aryl moiety being fluorine, chlorine, alkyl with up to 4 carbon atoms and alkoxy with up to 4 carbon atoms; R$^3$ is straight-chain or branched alkyl with 1 to 6, especially 1 to 4, carbon atoms, or cycloalkyl with 5 to 7, especially 5 to 6, carbon atoms, or can be hydrogen if R$^2$ does not denote hydrogen.

The compounds of the formula (I) possess two assymetrical carbon atoms and can therefore exist in the erythro form and in the threo form; in both cases they are predominantly obtained as racemates.

The present invention also provides a process for the preparation of a compound of the present invention, in which a 1-ethyl-imidazole of the general formula

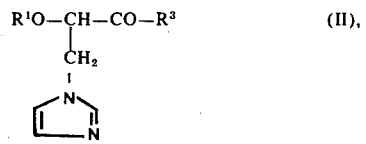

(II), in which
R$^1$ and R$^3$ have the above-mentioned meanings,
a. is reduced with hydrogen in the presence of a catalyst and optionally in the presence of a polar solvent, or
b. is reduced with aluminum isopropylate in the presence of a solvent, or
c. is reduced with a complex hydride, optionally in the presence of a polar solvent, or
d. is reduced with formamidinesulfinic acid and an alkali metal hydroxide, optionally in the presence of a polar solvent, or
e. is reacted with an organo-metallic compound of the general formula $$M\text{-}R^2 \quad (III),$$

in which
R$^2$ has the above-mentioned meaning (except hydrogen),
and
M is an alkali metal or the radical X-Mg
wherein
X is chlorine, bromine or iodine,
in the presence of an inert solvent,
the 1-propyl-imidazole derivative prepared in any of process variants (a) – (e) being converted, if desired, into a salt thereof.

If 2-p-chlorophenoxy-1-(imidazolyl-1')-4,4-dimethylpentan-3-one and hydrogen are used as starting materials in process variant (a), the course of the reaction can be represented by the following equation:

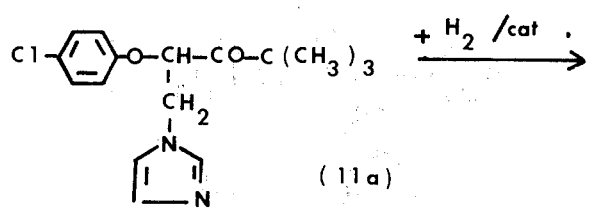

(IIa)

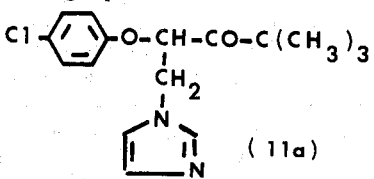
(1) (IV)

If 2-p-chlorophenoxy-1-(imidazolyl-1')-4,4-dimethylpentan-3-one and aluminum isopropylate are used as starting compounds in process variant (b), the course of the reaction can be represented by the following equation:

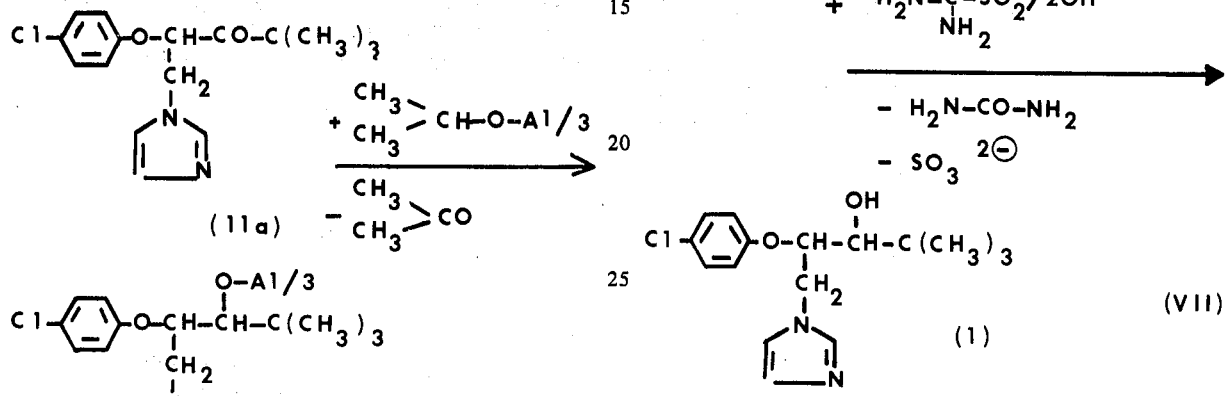
(V)

If 2-p-chlorophenoxy-1-(imidazolyl-1')-4,4-dimethylpentan-3-one and sodium borohydride are used as starting compounds in process variant (c), the course of the reaction can be represented by the following equation:

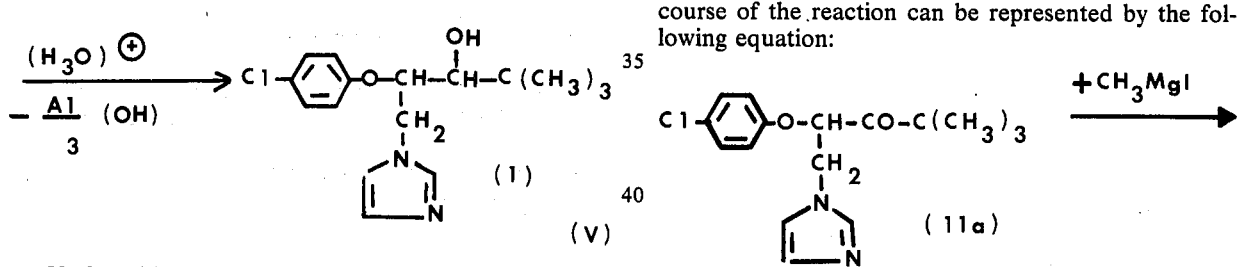
(VI)

If 2-p-chlorophenoxy-1-(imidazolyl-1')-4,4-dimethylpentan-3-one and formamidinesulfinic acid are used as starting compounds in process variant (d), the course of the reaction can be represented by the following equation:

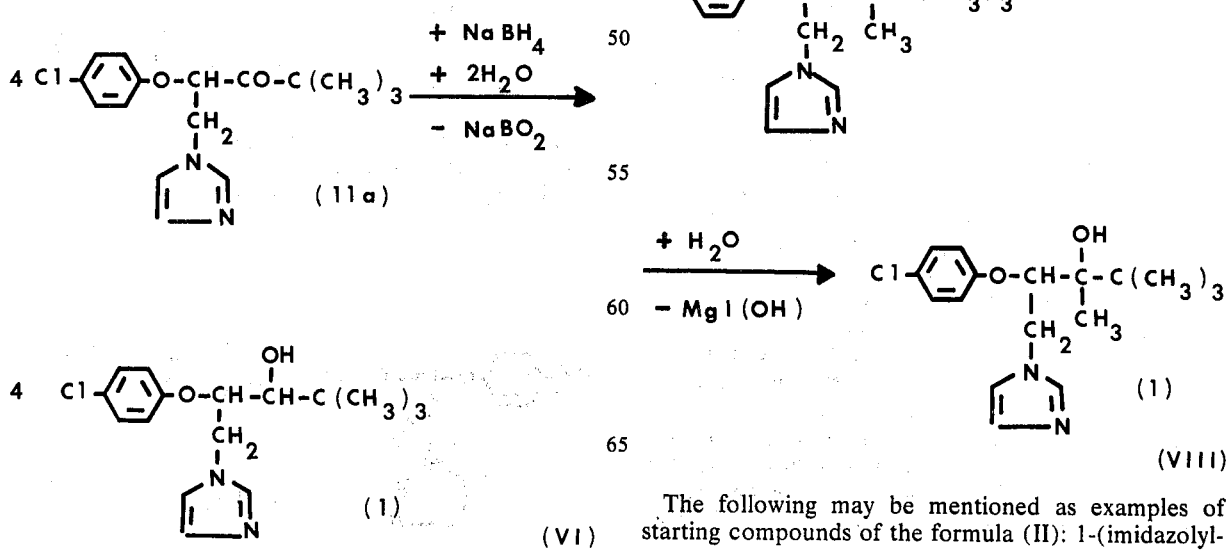

If 2-p-chlorophenoxy-1-(imidazolyl-1')-4,4-dimethylpentan-3-one and methyl-magnesium iodide are used as starting compounds in process variant (e), the course of the reaction can be represented by the following equation:

The following may be mentioned as examples of starting compounds of the formula (II): 1-(imidazolyl- 1′)-2-(p-chlorophenoxy)-4,4-dimethyl-pentan-3-one, 1-(imidazolyl-1′)-2-(m-chlorophenoxy)-4,4-dimethyl-pentan-3-one, 1-(imidazolyl-1′)-2-(3,4-dichlorophenoxy)-4,4-dimethyl-pentan-3-one, 1-(imidazolyl-1′)-2-(p-fluorophenoxy)-4,4-dimethyl-pentan-3-one, 1-(imidazolyl-1′)-2-(o-chlorophenoxy)-4,4-dimethyl-pentan-3-one, 1-(imidazolyl-1′)-2-(2-methyl-4-chlorophenoxy)-4,4-dimethyl-pentan-3-one and 1-(imidazolyl-1′)-2-phenoxy-3-cyclohexylpropan-3-one.

The 1-ethyl-imidazoles of the formula (II) which can be used according to the invention have not previously been described in the literature. However, they form the subject of application Ser. No. 390,042, filed Aug. 20, 1973, now pending, the disclosure of which is incorporated herein by reference, and can be prepared in accordance with the methods described there, either by reacting alkyl-(1-aryloxy-2-halogenoethyl)-ketones or alkyl-(1-aryloxy-2-hydroxyethyl)-ketones or corresponding aldehydes with imidazole, optionally in the presence of a high-boiling solvent, for example toluene, and in the presence of an acid-binding agent or agent which eliminates water, at temperatures of 80° to 150°C, or, in accordance with another process, by reacting alkyl-(1-aryloxy-1-halogenoethyl)-ketones or corresponding aldehydes with imidazole in a polar solvent, for example acetonitrile, in the presence of an acid-binding agent, at temperatures of 60° to 120°C. The compounds of the formula (II) are isolated, and purified, in the usual manner. In the second method for the synthesis of the 1-ethyl-imidazoles of the formula (II), 1-bromoethyl compounds are preferably employed. In this case, the imidazolyl radical does not react with the carbon atom which has lost the bromine atom, but with the adjacent carbon atom, and a compound of the general formula (II) is produced.

The alkyl-(1-aryloxy-2-hydroxyethyl)-ketones used, in the first-mentioned variant, as starting materials for the intermediates, have not previously been disclosed in the literature, but can be prepared according to generally customary methods. For example, they are obtained by condensing phenols or naphthols with halogenoketones in a known manner and reacting the resulting ether-ketone, in accordance with customary methods, in the presence of alkali, for example aqueous sodium hydroxide solution, with formaldehyde or a formaldehyde donor, for example a 40% strength aqueous formaldehyde solution, in an inert organic solvent, for example ethanol, at an elevated temperature, for example the boiling point of the reaction mixture, and isolating and purifying the desired products in the usual manner.

The alkyl-(1-aryloxy-2-halogenoethyl)-ketones used, in the first-mentioned variant, as starting materials for the intermediates, have also not previously been described, but can be prepared according to customary methods, for example by reacting a corresponding ether-ketone with formaldehyde or a formaldehyde donor in the presence of alkali, as explained above, and then reacting the resulting compound with a halogenating agent, such as thionyl chloride, in an inert polar organic solvent, such as, for example, methylene chloride, at room temperature, and isolating the desired end products in the usual manner and purifying them if appropriate.

The alkyl-(1-aryloxy-2-halogenoethyl)-ketones used in the second variant mentioned, as starting materials for the intermediates, have not previously been described but can be prepared according to generally customary methods, for example by reacting phenols or naphthols with a 1-halogenoethyl-ketone in the usual manner. The active α-hydrogen atom of the 1-aryloxyethyl-ketone thereby obtained is subsequently replaced by halogen in the usual manner, for example by means of elementary bromine in carbon tetrachloride at 40°–50°C. The desired product is isolated in a known manner and is purified if appropriate.

Preferred salts of the compounds of the formula (I) are salts with physiologically tolerated acids, especially the hydrogen halide acids, such as hydrobromic acid and, more especially, hydrochloric acid, phosphoric acid, monofunctional and bifunctional carboxylic acids and hydroxycarboxylic acids, such as acetic acid, maleic acid, succinic acid, fumaric acid, tartaric acid, citric acid, salicylic acid, sorbic acid and lactic acid, and 1,5-naphthalenedisulfonic acid.

Possible diluents for the reaction in accordance with process variant (a) are polar organic solvents, especially alcohols, such as methanol and ethanol, and nitriles, such as acetonitrile. The reaction is carried out in the presence of a catalyst. Preferably, noble metal catalysts, noble metal oxide catalysts (or noble metal hydroxide catalysts) or socalled "Raney catalysts" are used, especially platinum, platinum oxide and nickel. The reaction temperatures can be varied over a fairly wide range. In general, the reaction is carried out at between 20° and 50°C. Preferably at between about 20° and 40°C. The reaction can be carried out not only under normal pressure but also under elevated pressure, e.g. 1 to 2 atmospheres gauge. In the reaction according to variant (a), about 1 mole of hydrogen and about 0.1 mole of catalyst are generally employed per mole of the compound of the formula (II); to isolate the compounds, the catalyst is filtered off, the solvent is removed in vacuo and the resulting product of the formula (I) is purified by recrystallization. If desired, a salt of the compound thus prepared is obtained according to customary methods.

If variant (b) is employed, preferred diluents for the reaction according to the invention are alcohols, such as isopropanol, or inert hydrocarbons, such as benzene. The reaction temperatures can again be varied over a fairly wide range; in general, the reaction is carried out at between 20° and 120°C, preferably at about 50° to 100°C. To carry out the reaction, about 1 to 2 moles of aluminum isopropylate are generally employed per mole of the compound of the formula (II). To isolate the compound of the formula (I), the excess solvent is removed by distillation in vacuo and the resulting aluminum compound is decomposed with dilute sulfuric acid or sodium hydroxide solution. The further working up is carried out in the usual manner.

If variant (c) is employed, possible diluents for the reaction according to the invention are polar organic solvents, especially alcohols, such as methanol, ethanol, butanol and isopropanol, and ethers, such as diethyl ether or tetrahydrofuran. The reaction is generally carried out at from 0° to 30°C, preferably at about 0° to 20°C. About 1 mole of a complex hydride, such as sodium borohydride or lithium alanate, is generally employed per mole of the compound of the formula (II). To isolate the compound of the formula (I), the residue is taken up in dilute hydrochloric acid and the mixture is then rendered alkaline and extracted with an organic solvent. The further working up is carried out in the usual manner.

Possible diluents for the reaction in accordance with variant (d), are polar organic solvents, especially alcohols, such as methanol and ethanol, and also water. Here again, the reaction temperatures can be varied over a fairly wide range; the reaction is carried out at temperatures between 20° and 100°C, preferably at about 50° to 100°C. To carry out the reaction, about 1 to 3 moles of formamidinesulfinic acid and 2 to 3 moles of alkali metal hydroxide are employed per mole of the compounds of the formula (II). To isolate the end product, the reaction mixture is freed from the solvent and the residue is extracted with water and organic solvents, worked up in the usual manner and purified; a salt thereof may be prepared if desired.

In the reaction according to process variant (e), compounds of the general formula (I) in which $R^2$ is not hydrogen are obtained. In contrast, the reactions according to process variants (a) to (d) are reduction reactions; the compounds of the formula (I) thereby obtained are secondary alcohols in which $R^2$ in each case is only hydrogen.

M in the formula (III) is preferably lithium, sodium or a so-called "Grignard grouping" Mg-X, wherein X represents chlorine, bromine or iodine. Organo-metallic compounds of the formula (III) are known; a summary and survey of numerous publications is to be found, for example, in G. E. Coates "Organo-Metallic Compounds", 2nd edition, Methuen and Co., London (1960).

For the reaction in accordance with process variant (e), anhydrous ethers, such as diethyl ether, dibutyl ether and cyclic ethers, such as tetrahydrofuran, are preferentially employed. The reaction temperatures can be varied between about 0° and 80°C, preferably between 30° and 60°C. In carrying out process variant (e), about 1 mole of the organo-metallic compound of the formula (III) is generally employed per mole of the compound of the formula (II). The products obtained by organo-metallic reactions are worked up in the customary and generally known manner.

The active compounds according to the invention exhibit a strong fungitoxic action. They do not harm crop plants in the concentrations required to combat fungi. For these reasons, they are suitable for use as plant protection agents for combating fungi. Fungitoxic agents are employed in plant protection to combat Archimycetes, Phycomycetes, Ascomycetes, Basidiomycetes and *Fungi Imperfecti.*

The active compounds according to the invention have a very broad spectrum of action and can be used against parasitic fungi which attack above-ground parts of plants or which attack the plants through the soil, and against seed-borne pathogens.

The active compounds exhibit a particularly good action against parasitic fungi on above-ground parts of plants, such as species of Erysiphe, species of Fusicladium, species of Podosphaera, species of Venturia and also species of Pyricularia and species of Pellicularia.

It should be emphasised that the active compounds according to this invention not only exhibit a protective action but are also curatively active, that is to say can also be employed after infection has taken place. Furthermore, the systemic action of the compounds should be pointed out. Thus it proves possible to protect plants against fungal attack by supplying the active compound to the above-ground parts of plants through the soil, through the plant or through the seed. As plant protection agents, the active compounds according to the invention can be used for the treatment of seed and for the treatment of above-ground parts of plants.

The compounds according to the invention are well tolerated by plants. They have only a low toxicity towards warm-blooded animals and because of their low odor and their good toleration by human skin they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, rodenticides, bactericides, nematocides, herbicides, fertilizers, growth-regulating agents, bird repellents, plant nutrients, agents for improving the soil structure, etc., if desired, or in the form of particular dosage preparations for specific application made therefrom, such as solutions, emulsions, suspensions, powders, pastes, and granules which are thus ready for us.

As concerns commercially marketed preparations, these generally contemplate carrier composition mixtures in which the active compound is present in an amount substantially between about 0.1–95% by weight, and preferably 5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Especially when used as leaf fungicides, the concentrations of active compound in the use forms can be varied within a fairly wide range. In general, the concentrations are from 0.1 to 0.00001 per cent by weight, preferably from 0.05 to 0.0001 per cent.

In treatment of seed, amounts of active compound of 0.001 to 50 g, preferably 0.01 to 10 g, per kilogram of seed are required in general.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples.

EXAMPLE 1

Fusicladium test (apple scab)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Yound apple seedlings in the 4 – 6 leaf stage were sprayed with the spray liquid until dripping wet. The plants remained in a greenhouse for 24 hours at 20°C and at a relative atmospheric humidity of 70%. They were then inoculated with an aqueous conidium suspension of the apple scab causative organism (*Fusicladium dendriticum Fuckel*) and incubated for 18 hours in a humidity chamber at 18° – 20°C and at a relative atmospheric humidity of 100%.

The plants were again brought into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compounds, the concentrations of the active compounds and the results can be seen from the following table.

Table 1
Fusicladium test/protective

| Active compound | | Infection in % of the infection of the untreated control at an active compound concentration of 0.01% |
|---|---|---|
| $H_5C_6-\underset{\underset{C_6H_5}{\mid}}{\overset{\overset{\text{imidazole}}{\mid}}{C}}-C_6H_5$ | (known) (A) | 75 |
| $F-\underset{}{C_6H_4}-O-CH-\underset{\underset{\text{imidazole}}{\mid}}{\overset{\overset{OH}{\mid}}{CH}}-C(CH_3)_3$ with $CH_2$ | (6) | 20 |

Table 2
Erysiphe test/systemic

| Active compound | | Infection in % of the infection of the untreated control at an active compound concentration of 100 ppm |
|---|---|---|
| $H_5C_6-\underset{\underset{C_6H_5}{\mid}}{\overset{\overset{\text{imidazole}}{\mid}}{C}}-C_6H_5$ | (known) | 75 |
| $F-C_6H_4-O-CH-\overset{\overset{OH}{\mid}}{CH}-C(CH_3)_3$ with $CH_2$-imidazole | (6) | 0 |

EXAMPLE 3

Shoot treatment test/powdery mildew of cereals/protective (Leaf-destructive mycosis)

To produce a suitable preparation of active compound, 0.25 part by weight of active compound was taken up in 25 parts by weight of dimethylformamide and 0.06 part by weight of emulsifier W and 975 parts by weight of water were added. The concentrate was diluted with water to the desired final concentration.

To test for protective activity, single-leaved young barley plants of the Amsel variety were sprayed with the preparation of active compound until dew-moist. After drying, the young barley plants were dusted with spores of Erysiphe graminis var. hordei.

EXAMPLE 2

Erysiphe test/systemic
Solvent: 4.7 parts by weight of acetone
Emulsifier: 0.3 part by weight of alkylaryl polyglycol ether
Water: 95 parts by weight The amount of active compound required to give the desired concentration of active compound in the watering liquid was mixed with the stated amount of solvent and the concentrate was diluted with the stated amount of water which contained the stated additives.

Cucumber plants grown in standard soil, in the 1-2 leaf stage, were watered once within one week with 20 ml of the watering liquid, of the stated concentration of active compound, per 100 ml of soil.

The plants treated in this way were inoculated, after treatment, with conidia of the fungus Erysiphe cichoracearum. The plants were then set up in a greenhouse at 23°–24°C and 70% relative atmospheric humidity. After 12 days, the infection of the cucumber plants was determined as a percentage of the untreated, but also inoculated, control plants.

0% denotes no infection and 100% denotes that the infection was exactly as great as in the case of the control plants.

The active compounds, active compound concentrations and results can be seen from the table which follows.

After 6 days' dwell time of the plants at a temperature of 21°–22°C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of mildew infection.

The active compounds, active compound concentrations in the spray liquor and degrees of infection can be seen from the table which follows:

Table 3

Shoot treatment test/powdery mildew of cereals/protective

| Active compound | | Active compound concentration in the spray liquor in % by weight | Infection in % of the untreated control |
|---|---|---|---|
| Untreated | | — | 100.0 |
| [structure: CH₂–NH–C(=S)–S / CH₂–NH–C(=S)–S \ Zn] | (known) (C) | 0.025 0.01 | 100.0 100.0 |
| [structure: Cl–C₆H₄–C(–C₆H₅)(–N imidazole)–C₆H₄–Cl] | (known) (B) | 0.01 | 82.5 |
| [structure: 2,4-Cl₂–C₆H₃–O–CH(CH₂-imidazole)–CH(OH)–C(CH₃)₃] | (5) | 0.01 | 3.8 |
| [structure: 4-F–C₆H₄–O–CH(CH₂-imidazole)–CH(OH)–C(CH₃)₃] | (6) | 0.01 0.001 | 25.0 25.0 |
| [structure: 4-Cl–C₆H₄–O–CH(CH₃)–C(CH₂OH)(N-imidazole)–C(CH₃)₃] | (9) | 0.01 | 33.8 |
| [structure: 4-Cl–C₆H₄–O–CH(CH₂-imidazoline)–CH(OH)–C(CH₃)₃] | (1) | 0.01 | 28.8 |

EXAMPLE 4

Shoot treatment test/powdery mildew of cereals/curative (leaf-destructive mycosis)

The active compounds, active compound concentrations in the spray liquor and degrees of infection can be seen from the table which follows:

Table 4

Shoot treatment test/powdery mildew of cereals/curative (leaf-destructive mycosis)

| Active compounds | | Active compound concentration in the spray liquor in % by weight | Infection in % of the untreated control |
| --- | --- | --- | --- |
| Untreated | | — | 100.0 |
| CH₂—NH—C(=S)—S \ Zn / CH₂—NH—C(=S)—S | (known) (C) | 0.025 | 100.0 |
| triphenyl-imidazolyl-methane structure | (known) (A) | 0.01 0.005 | 87.5 100.0 |
| F-C₆H₄-O-CH(CH₂-imidazolyl)-CH(OH)-C(CH₃)₃ | (6) | 0.01 0.005 | 0.0 0.0 | tive (leaf-destructive mycosis)

To produce a suitable preparation of active compound, 0.25 part by weight of active compound was taken up in 25 parts by weight of dimethylformamide and 0.06 part by weight of emulsifier W and 975 parts by weight of water were added. The concentrate was diluted with water to the desired final concentration of the spray liquor.

To test for curative activity the procedure followed was analogous to the test for protective activity, but in the converse sequence. The treatment of the single-leaved young barley plants with the preparation of the active compound was carried out 48 hours after inoculation, when the infection was already manifest.

After 6 days' dwell time of the plants at a temperature of 21–22°C and 80–90% atmospheric humidity the occurrence of mildew pustules on the plants was evaluated. The degree of infection was expressed as a percentage of the infection of the untreated control plants. 0% denotes no infection and 100% denotes the same degree of infection as in the case of the untreated control. The more active the compound, the lower is the degree of mildew infection.

The process of this invention is illustrated by the following preparative Examples.

EXAMPLE 5

(A) 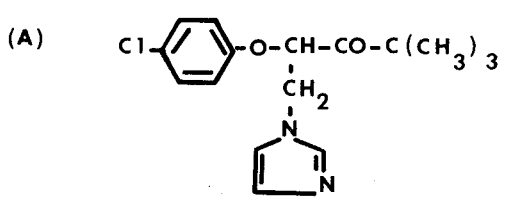

The starting material, 2-(p-chlorophenoxy)-2-bromo-4,4-dimethyl-pentan-3-one, was obtained by bromination of 2-(p-chlorophenoxy)-4,4-dimethyl-pentan-3-one with elementary bromine in carbon tetrachloride at 40°–50°C; melting point: 95°C.

16.0 g (0.05 mole) of 2-(p-chlorophenoxy)-2-bromo-4,4-dimethyl-pentan-3-one in 120 ml of acetonitrile were heated with 12 g (0.207 mole) of imidazole for 12 hours to the boil under reflux. The solvent was then distilled off in vacuo until the mixture was almost reduced to dryness and 50 ml of ether and 50 ml of a saturated solution of hydrogen chloride in ether were then added. The resulting oil was decanted off and boiled up three times with 50 ml of ether each time, and the ether phase was decanted off. The oil which remained was taken up in 120 ml of methylene chloride, then 50 ml of water and 20 g of solid sodium bicarbonate were added, the organic phase was separated off and the aqueous phase was twice extracted with 50 ml of methylene chloride. The combined organic phases were twice washed with 50 ml of water, dried over sodium sulfate and distilled off in vacuo. The oil obtained was triturated with ligroin/petroleum ether, whereupon it crystallized. After recrystallization from ligroin/petroleum ether, 2.6 g of 1-(imidazolyl-1')-2-(p-chlorophenoxy)-4,4-dimethyl-pentan-3-one (representing 17% of theory) of melting point 68°–73°C were obtained.

b. 1-(Imidazolyl-1')-2-(p-chlorophenoxy)-4,4-dimethyl-pentan-3-one could, however, also be prepared by dissolving 22.6 g (0.1 mole) of 1-(p-chlorophenoxy)-3,3-dimethyl-butan-2-one in 200 ml of ethanol and adding 20 g (0.24 mole) of 40 percent strength formaldehyde solution followed by about 5 ml of 10% strength sodium hydroxide solution until the pH was 9. The reaction mixture was heated under reflux for 3 hours and the solvent was distilled off in vacuo. The resulting precipitate was filtered off and well rinsed with petroleum ether. The filtrate was concentrated in vacuo. An oil remained; this was crude 2-(p-chlorophenoxy)-1-hydroxy-4,4-dimethyl-pentan-3-one.

25.6 g (0.1 mole) of 2-(p-chlorophenoxy)-1-hydroxy-4,4-dimethyl-pentan-3-one were taken up in 200 ml of toluene, 10.2 g (0.14 mole) of imidazole were added dropwise and the reaction solution was boiled under a water separator for 3 hours. The solvent was then distilled off in vacuo, 100 ml of water were added to the resulting oil and the mixture was twice extracted with 100 ml of methylene chloride. The organic phase was twice washed with 50 ml of water and dried over sodium sulfate and the solvent was distilled off in vacuo. An oil was obtained, which was taken up in 50 ml of ether and mixed with 50 ml of ether saturated with dry hydrogen chloride. The solvent was distilled off in vacuo and the resulting oil was taken up in the mixture of 500 ml of ligroin and 300 ml of ethyl actetate and heated to the boil under reflux. After carefully decanting the resulting solution and cooling it, 16.8 g (49% of theory) of 1-(imidazolyl-1')-2-(p-chlorophenoxy)-4,4-dimethylpentan-3-one hydrochloride precipitated and were filtered off. The base could be obtained from this material in the usual manner, for example by dissolving in water, rendering alkaline and extraction with ether or ethyl acetate.

15.3 g (0.05 mole) of 1-(imidazolyl-1')-2-(p-chlorophenoxy)-4,4-dimethyl-pentan-3-one were dissolved in 150 ml of methanol. 2.9 g (0,08 mole) of sodium borohydride were added thereto at 0° to 5°C and the mixture was stirred overnight at room temperature. It was then cautiously acidified with 10 ml of concentrated hydrochloric acid and the reaction mixture was again stirred overnight at room temperature and was poured into 250 ml of saturated sodium bicarbonate solution. After extraction with twice 100 ml of methylene chloride, the organic phase was washed with twice 100 ml of water and dried over sodium sulphate, and the solvent was distilled off under reduced pressure. The crystalline residue was boiled up with 100 ml of cyclohexane, filtered off hot and dried. 13.4 g (87% of theory) of 1-(imidazolyl-1')-2-(p-chlorophenoxy)-4,4-dimethyl-pentan-3-ol of melting point 163° to 170°C were obtained.

EXAMPLE 6

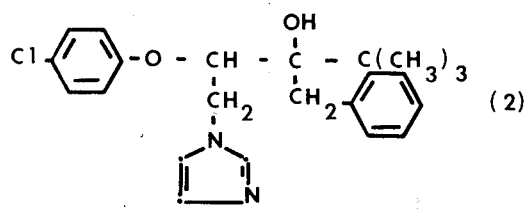
(2)

A solution of 10.7 g (0.1 mole) of benzyl chloride in 50 ml of anhydrous ether was added dropwise to a suspension of 2.4 g (0.1 mole) of magnesium filings in 30 ml of anhydrous benzene in such a way as to cause a slow but steady reaction. When all the benzyl chloride had been added, the reaction was allowed to continue for a further 30 minutes and a solution of 15.3 g (0.05 mole) of 1-(imidazolyl-1')-2-(p-chlorophenoxy)-4,4-dimethyl-pentan-3-one in 250 ml of anhydrous tetrahydrofurane was then added dropwise. After heating for 15 hours under reflux, the solution was cooled and then stirred into 500 ml of aqueous 10 per cent strength ammonium chloride solution, and 50 ml of concentrated ammonia solution were added. After stirring for half an hour at room temperature, 100 ml of ethyl acetate were added and the organic phase was separated off, washed four times with 50 ml of water, dried over sodium sulfate and freed from the solvent in vacuo. The residue was boiled up with 100 ml of cyclohexane, filtered off hot and dried. 12.5 g (63% of theory) of 1-(imidazolyl-1')-2-(p-chlorophenoxy)-3-benzyl-4,4-dimethyl-pentan-3-ol of melting point 179° to 181°C were obtained.

The following compounds of the general formula (C)

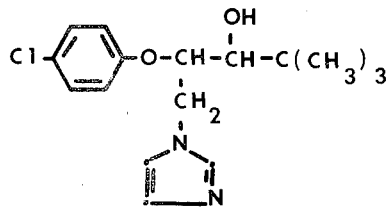
(1)

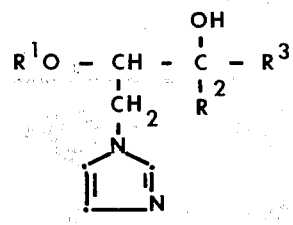

were prepared analogously:

| Compound No. | R¹ | R² | R³ | Melting point, °C |
|---|---|---|---|---|
| 3 | 2-Cl-C₆H₄- | H | C(CH₃)₃ | 162 – 163 |
| 4 | 3-Cl-C₆H₄- | H | C(CH₃)₃ | 132 – 133 |
| 5 | 2,6-Cl₂-C₆H₃- | H | C(CH₃)₃ | 198 – 202 |
| 6 | 4-F-C₆H₄- | H | C(CH₃)₃ | 146 – 148 |
| 7 | 2-Cl-6-CH₃-C₆H₃- | H | C(CH₃)₃ | 163 – 164 |
| 8 | C₆H₅- | H | C(CH₃)₃ | 118 |
| 9 | 4-Cl-C₆H₄- | CH₃ | C(CH₃)₃ | 155 |
| 10 | 4-Cl-C₆H₄- | C₆H₅- | H | 145 – 148 |
| 11 | C₆H₅- | C₆H₅- | H | 116 |
| 12 | 4-Cl-C₆H₄- | 4-Cl-C₆H₄- | H | 160 – 165 |
| 13 | 2,4-Cl₂-C₆H₃- | 4-Cl-C₆H₄- | H | 110 – 114 |

It will be appreciated that the instant specification and examples are set forth by way of illustration and not limitation, and that various modifications and changes may be made without departing from the spirit and scope of the present invention.

Other compounds which may be similarly prepared include:

| R¹ | R² | R³ |
|---|---|---|
| -C₆H₄-Cl | -CH₂-C₆H₄-Cl | H |
| 3-OCH₃-C₆H₄- | H | C(CH₃)₃ |

—Continued

| R¹ | R² | R³ |
|---|---|---|
| -C₆H₄-NO₂ | H | -C₆H₁₁ |
| -C₆H₄-SO₂CH₃ | -CH₂-C₆H₄-OCH₃ | H |
| -C₆H₄-NH₂ | H | C(CH₃)₃ |
| -C₆H₄-CO-OC₂H₅ | H | C(CH₃)₃ |

What we claim is:

1. A 1-(imidazolyl-1')-2-aryloxy-3-hydroxy alkane of the formula

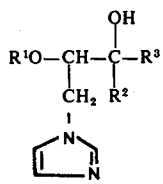

in which
R¹ is an optionally monosubstituted or disubstituted phenyl or naphthyl radical with 6 to 10 carbon atoms, the substituents being selected from halogen, straight-chain or branched alkyl with 1 to 6 carbon atoms, alkoxy, alkylthio and alkylsulfonyl each with 1 to 4 carbon atoms, halogenoalkyl with 1 to 2 carbon atoms and 1 to 5 halogen atoms, halogenoalkoxy and halogenoalkylthio each with 1 or 2 carbon atoms and 3 to 5 halogen atoms, alkoxycarbonyl with 1 to 4 carbon atoms in the alkoxy moiety, phenyl in the o- and p- position, amino and nitro;
R² is alkyl with up to 6 carbon atoms, or phenylalkyl or naphthylalkyl with 1 or 2 carbon atoms in the alkyl moiety and which may be monosubstituted on the phenyl or naphthyl moiety by fluorine, chlorine, alkyl with up to 4 carbon atoms or alkoxy with up to 4 carbon atoms;
R³ is straight-chain or branched alkyl with 1 to 6 carbon atoms, or hydrogen,
or a salt thereof with fungicidal activity.

2. The compound according to claim 1 wherein such compound is 1-(imidazolyl-1')-2-(2,4-dichlorophenoxy)-4,4-dimethyl-pentan-3-ol of the formula

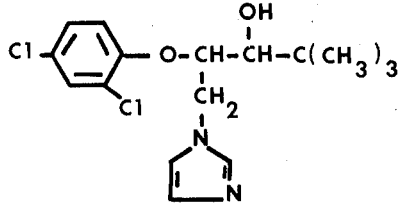

3. The compound according to claim 1, wherein such compound is 1-(imidazolyl-1')-2-(p-fluorophenoxy)-4,4-dimethyl-pentan-3-ol of the formula

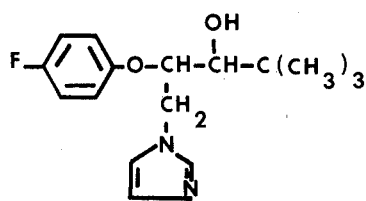

4. The compound according to claim 1 wherein such compound is 1-(imidazolyl-1')-2-(p-chlorophenoxy)-3,4,4-trimethyl-pentan-3-ol of the formula 5. The compound according to claim 1 wherein such compound is 1-(imidazolyl-1')-2-(p-chlorophenoxy)-3-(p-chlorophenyl)-propan-3-ol of the formula

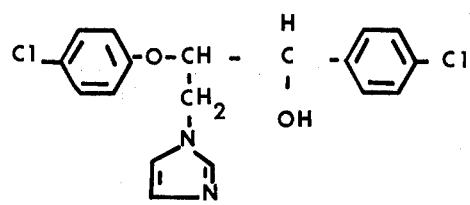

* * * * *

UNITED STATES PATENT AND TRADEMARK OFFICE
CERTIFICATE OF CORRECTION

PATENT NO. : 3,940,415
DATED : February 24, 1976
INVENTOR(S) : Karl-Heinz Buchel, et al.

It is certified that error appears in the above-identified patent and that said Letters Patent are hereby corrected as shown below:

Col. 11, line 65 through Col. 13, line 6

Delete "EXAMPLE 2.....can be seen from the table which follows: " and insert in Col. 11, following Table 1 and preceding Table 2.

Signed and Sealed this twenty-third Day of August 1977

[SEAL]

Attest:

RUTH C. MASON
Attesting Officer

C. MARSHALL DANN
Commissioner of Patents and Trademarks